United States Patent
Kikuchi et al.

(10) Patent No.: US 11,591,297 B2
(45) Date of Patent: Feb. 28, 2023

(54) COMPOUND HAVING PD-L1 EXPRESSION-SUPPRESSING ACTION

(71) Applicants: TOHOKU UNIVERSITY, Sendai (JP); JUNSEI EDUCATIONAL INSTITUTION, Okayama (JP); FUSO PHARMACEUTICAL INDUSTRIES, LTD., Osaka (JP)

(72) Inventors: Haruhisa Kikuchi, Tokyo (JP); Yoshiteru Oshima, Sendai (JP); Toshio Hattori, Takahashi (JP); Osamu Yamada, Osaka (JP); Jing Zhang, Osaka (JP); Shinya Kida, Osaka (JP); Shinya Murase, Osaka (JP)

(73) Assignees: TOHOKU UNIVERSITY, Sendai (JP); JUNSEI EDUCATIONAL INSTITUTION, Okayama (JP); FUSO PHARMACEUTICAL INDUSTRIES, LTD., Osaka (JP)

(*) Notice: Subject to any disclaimer, the term of this patent is extended or adjusted under 35 U.S.C. 154(b) by 0 days.

(21) Appl. No.: 17/602,331

(22) PCT Filed: Apr. 8, 2020

(86) PCT No.: PCT/JP2020/015771
§ 371 (c)(1),
(2) Date: Oct. 8, 2021

(87) PCT Pub. No.: WO2020/209277
PCT Pub. Date: Oct. 15, 2020

(65) Prior Publication Data
US 2022/0194900 A1    Jun. 23, 2022

(30) Foreign Application Priority Data
Apr. 9, 2019 (JP) .............................. JP2019-074077

(51) Int. Cl.
*C07D 211/60* (2006.01)
*A61P 35/00* (2006.01)

(52) U.S. Cl.
CPC ............ *C07D 211/60* (2013.01); *A61P 35/00* (2018.01)

(58) Field of Classification Search
None
See application file for complete search history.

(56) References Cited

U.S. PATENT DOCUMENTS
2015/0087673 A1    3/2015    Hitoshi et al.

OTHER PUBLICATIONS

EPO Extended European Search Report for corresponding EP Application No. 20787629.3; dated May 11, 2022.

Tryfon Zarganes-Tzitzikas et al., "Inhibitors of programmed cell death 1 (PD-1): a patent review (2010-2015)", Expert Opinion on Therapeutic Patents, vol. 26, No. 9, Sep. 19, 2016, pp. 973-977.

Bell, J. L. et al., "Optimization of novel nipecotic bis(amide) inhabitors of the Rho/MKL1/SRF transcriptional pathway as potential anti-metastasis agents," Bioorganic & Medicinal Chemistry Letters, 2013, vol. 23,pp. 3826-3832.

Boni, C. et al., "Characterization of Hepatitis B Virus (HBV)-Specific T-Cell Dysfunction in Chronic HBV Infection," Journal of Virology, vol. 81, No. 8, Apr. 2007, pp. 4215-4225.

Cho, K. et al., "Targeting the Cyclophilin Domain of Ran-binding Protein 2 Ranbp2) with Novel Small Molecules to Control the Proteostasis of STAT3, hnRNPA2B1 and M-Opsin," ACS Chemical Neuroscience, 2015, vol. 6, pp. 1476-1485.

He, J. et al., "Development of PD-1/PD-L1 Pathway in Tumor Immune Microenvironment and Treatment for Non-Small Cell Lung Cancer," Scientific Reports, vol. 5-13110,, 2015; pp. 1-9.

International Preliminary Report of Patentability (Chapter II) for International Application No. PCT/JP2020/015771; dated Oct. 14, 2021.

International Search Report and Written Opinion of the International Searching Authority for International Application No. PCT/JP2020/015771; dated Jul. 7, 2020.

Yao, Z. Q. et al., "T Cell Dysfunction by Hepatitis C Virus Core Protein Invoilves PD-1/PDL-1 Signaling," Viral Immunology, vol. 20, No. 2, 2007, pp. 276-287.

Kato, T. et al., "Exhaustion of CMV Specific T Cells with Enhanced PD-1 Expression In Persistent Cytomegalovirus Infection After Allogeneic Stem Cell Transplantation," Blood, 116 (Nov. 19, 2010) (21):3912; 3 pages.

Liu, C. et al., "Increased expression of PD-L1 by the human papillomavirus 16 E7 oncoprotein inhibits anticancer immunity," Molecular Medicine Reports, 15: pp. 1063-1070 (2015).

Ma, S-D.et al., "PD-1/CTLA-4 Blockade Inhibits Epstein-Barr Virus-Induced Lymphoma Growth in a Cord Blood Humanized-Mouse Model," PloS Pathogens, 12 (May 17, 2016), e1005642; 23 pages.

Mitobe, Y. K. et al., "The Roles of Coinhibitory Receptors in Pathogenesis of Human Retroviral Infections," Frontiers in Immunology, vol. 9, Nov. 27, 2018, doi:10.3389; 8 pages.

Sakai, S. et al., "PD-1-PD-L1 pathway impairs Th1 immune response in the late stage of infection with *Mycobacterium bovis* bacillus Calmette-Guerin," International Immunology, vol. 22, No. 12, Nov. 3, 2010, pp. 915-925.

(Continued)

*Primary Examiner* — Brian J Davis
(74) *Attorney, Agent, or Firm* — Cantor Colburn LLP (57) ABSTRACT

The present invention provides a compound of formula (I):

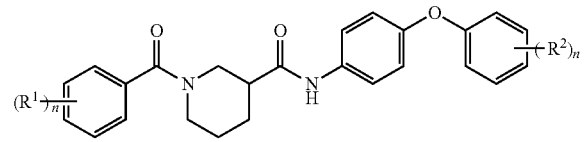

or a pharmaceutically acceptable salt thereof, wherein $R^1$, $R^2$, m and n are as defined in the specification, with an inhibitory effect of PD-L1 expression and an inhibitory effect of reduced production of IL-2 and a medicament useful for the treatment of a disease associated with the reduced immune function caused by the formation of PD-1/PD-L1 binding.

20 Claims, 2 Drawing Sheets

(56) References Cited

OTHER PUBLICATIONS

Skalniak, L. et al., "Small-molecule inhibitors of PD-1/PD-L1 immune checkpoint alleviate the PD-L1-induced exhaustion of T-cells," Oncotarget, vol. 8, No. 42, 2017, pp. 72167-72181.
STN Registry File, Sep. 23, 2004, RN 749906-44-3, [online], retrieved on Jun. 9, 2020.
STN Registry File, Dec. 7, 2004, RN 793690-54-7, [online], retrieved on Jun. 9, 2020.
STN Registry File, Jun. 7, 2005, RN 851790-66-4, [online], retrieved on Jun. 9, 2020.
STN Registry File, Mar. 5, 2018, RN 2184375-28-6, [online], retrieved on Jun. 9, 2020.
STN Registry File, Apr. 6, 2018, RN 2207120-10-1, [online], retrieved on Jun. 9, 2020.

COMPOUND HAVING PD-L1 EXPRESSION-SUPPRESSING ACTION

CROSS REFERENCE TO RELATED APPLICATIONS

This is the U.S. national stage of application No. PCT/JP2020/015771, filed on Apr. 8, 2020. Priority under 35 U.S.C. § 119(a) and 35 U.S.C. § 365(b) is claimed from Japanese Application No. 2019-074077, filed Apr. 9, 2019, the disclosure of which is also incorporated herein by reference.

TECHNICAL FIELD

The present invention relates to a novel compound with an inhibitory effect of PD-L1 expression, specifically 1-benzoyl-N-(4-phenoxyphenyl)piperidine-3-carboxamide compound. Also, the present invention can be used in the treatment of a disease associated with the reduced immune function caused by the formation of PD-1/PD-L1 binding.

BACKGROUND ART

Organisms have not only immune systems to protect themselves from foreign pathogens and cancer cells arising from their own bodies but also immunoregulatory systems to prevent disorders to themselves caused by hyperimmunization. Recently, it has been revealed that cancer cells induce the immunoregulatory systems in the tumor microenvironment to escape from the immune systems of organisms. One example of the mechanisms include tumor immune escape produced by the effect of PD-1 or PD-L1 referred to as "immune checkpoint molecules" (Non-Patent Document 1).

When cancer cells are repeatedly attacked from killer T-cells which are one of immunocompetent cells, the cancer cells receive interferon-γ (IFN-γ) released from T-cells and express PD-L1 on the cell surface. When the expressed PD-L1 is bound to PD-1 expressed in T-cells, the production amount of interleukin-2 (IL-2) that enhances the proliferation of T-cells is reduced and the apoptosis (cell death) of T-cells is induced, and thus the cancer cells can escape from the attack of T-cells. On the other hand, new types of anti-cancer agents capable of specifically binding to PD-1 or PD-L1 and inhibiting the formation of PD-1/PD-L1 binding between T cells and cancer cells have already been approved, and the agents are referred to as an inhibitor of immune checkpoint.

Methods of treating cancer are mainly surgical, chemical, and radiation therapies, but there have not been any established treatment methods which can bring in some sufficient effect yet, thus it is desired to establish novel treatment methods. PD-1 and PD-L1 have been a new target for treating cancer as molecules which inhibitively act on immunity ("immune checkpoint molecules").

In addition, it has been reported that in the infection caused by pathogens, for example, bacteria such as tuberculosis and virus such as hepatitis B virus, papillomavirus, killer T cells highly express PD-1 in the late stage of infections and antigen presenting cells (macrophages and dendritic cells) express PD-L1, and thus PD-1/PD-L1 binding is formed and the formed PD-1/PD-L1 binding causes the reduced immune function, resulting in infection (Non-Patent Documents 2-8).

Hence, it is thought that targeting PD-1 and/or PD-L1 leads to the treatment of a disease associated with the reduced immune function caused by the formation of PD-1/PD-L1 binding, for example, cancer and infection.

Anti-PD-1 antibody (nivolumab, pembrolizumab) and anti-PD-L1 antibody (atezolizumab, durvalumab) have already been developed as an inhibitor of immune checkpoint which targets PD-1 or PD-L1 so far. However, these agents are antibody drugs, and thus cannot be administered orally and are expensive in terms of cost, unlike small molecule drugs. As a result, the development of an inhibitor of immune checkpoint for small molecule compounds targeting PD-1 or PD-L1 that can be administered orally and formulated at low cost is expected (Non-Patent Document 9). However, no small molecule compound useful as an inhibitor of immune checkpoint targeting them has been known yet.

PRIOR ART DOCUMENTS

Non-Patent Documents

Non-Patent Document 1: He, J. et al. Sci Rep 5 (2015), 13110, pp 1-9
Non-Patent Document 2: Sakai, S. et al. Int Immunol 22 (2010), pp. 915-925
Non-Patent Document 3: Boni, C. et al. J Vorol 81 (2007), pp. 4215-4225
Non-Patent Document 4: Liu, C. et al. Mol Med Rep (2015), pp. 1063-1070
Non-Patent Document 5: Yao, Z. Q. et al. Viral Immunol 20 (2007), pp 276-286
Non-Patent Document 6: Motobe, Y. K. et al. Front Immunol 9 (2018), doi: 10.3389
Non-Patent Document 7: Kato, T. et al. Blood 116 (2010), pp 3912
Non-Patent Document 8: Ma, S-D. et al. Plos Pathog 12 (2016), e1005642
Non-Patent Document 9: Skalniak, L. et al., Oncotarget 8 (2017), pp. 72167-72181

SUMMARY OF INVENTION

Problem to be Solved by the Invention

An object of the present invention is to study a small molecule compound with inhibitory activities of PD-L1 expression and reduced IL-2 production and to provide a medicament useful for the treatment of a disease associated with the reduced immune function caused by the formation of PD-1/PD-L1 binding (e.g., an inhibitor of immune checkpoint) and a vaccine adjuvant therefor.

Means for Solving the Problems

The present inventors have extensively studied to reach the above object, and then have found that a compound of the following formula (I) and a pharmaceutically acceptable salt thereof (hereinafter, also referred to as "the compound (s) of the present invention") have an inhibitory effect of PD-L1 expression and an inhibitory effect of reduced production of IL-2. Based on the findings, the present invention has been completed. Since the compound of the present invention acts as an inhibitor of immune checkpoint because of the inhibitory effect of PD-L1 expression, the present invention can treat a disease associated with the reduced immune function caused by the formation of PD-1/PD-L1 binding, for example, cancer and infection.

That is, the present invention provides the following embodiments.

[1] A compound of formula (I):

or a pharmaceutically acceptable salt thereof, wherein $R^1$ and $R^2$ are each independently selected from the group consisting of halogen, hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro, amino, mono- or di-$C_{1-6}$ alkylamino, pentafluorosulfanyl, aryl and heteroaryl, wherein said aryl and heteroaryl may be optionally substituted with one group or the same or different two or more groups selected independently from the group consisting of halogen, hydroxy, cyano, nitro, amino, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, $C_{1-6}$ haloalkoxy and $C_{1-6}$ hydroxyalkoxy at any replaceable positions;

m is an integer of 0 to 5; and n is an integer of 0 to 5.

[2] The compound according to [1] or a pharmaceutically acceptable salt thereof, wherein $R^1$ and $R^2$ are each independently selected from the group consisting of halogen, hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro and pentafluorosulfanyl;

m is 1 or 2; and n is 1 or 2.

[3] The compound according to [1] or [2] or a pharmaceutically acceptable salt thereof, wherein $R^1$ is each independently selected from hydroxy, $C_{1-6}$ alkyl, $C_{1-6}$ alkoxy or nitro; and $R^2$ is each independently selected from halogen, $C_{1-6}$ alkyl, $C_{1-6}$ haloalkyl, $C_{1-6}$ alkoxy or pentafluorosulfanyl.

[4] The compound according to any of [1] to [3] or a pharmaceutically acceptable salt thereof, wherein $R^1$ is hydroxy, $C_{1-6}$ alkoxy or nitro which is linked at the 3- and/or 4-positions of the benzene ring.

[5] The compound according to any of [1] to [4] or a pharmaceutically acceptable salt thereof, wherein $R^2$ is $C_{1-6}$ haloalkyl or pentafluorosulfanyl which is linked at the 4-position of the benzene ring.

[6] The compound according to any of [1] to [5] or a pharmaceutically acceptable salt thereof selected from
1-(4-hydroxybenzoyl)-N-(4-(4-(trifluoromethyl)phenoxy)phenyl)piperidine-3-carboxamide,
1-(4-nitrobenzoyl)-N-(4-(4-(trifluoromethyl)phenoxy) phenyl)piperidine-3-carboxamide,
1-(4-hydroxy-3-methoxybenzoyl)-N-(4-(4-(trifluoromethyl)phenoxy)phenyl)piperidine-3-carboxamide,
1-(4-hydroxybenzoyl)-N-(4-(4-pentafluorosulfanyl) phenoxy)phenyl)piperidine-3-carboxamide,
1-(4-nitrobenzoyl)-N-(4-(4-(pentafluorosulfanyl) phenoxy) phenyl)piperidine-3-carboxamide, or
1-(4-hydroxy-3-methoxybenzoyl)-N-(4-(4-(pentafluorosulfanyl)phenoxy)phenyl)piperidine-3-carboxamide.

[7] A pharmaceutical composition comprising the compound according to any of [1] to [6] or a pharmaceutically acceptable salt thereof and a pharmaceutically acceptable carrier.

[8] The pharmaceutical composition according to [7] for treating a disease associated with the reduced immune function caused by the formation of PD-1/PD-L1 binding.

[9] The pharmaceutical composition according to [8], wherein the disease associated with the reduced immune function caused by the formation of PD-1/PD-L1 binding is cancer or infection.

[10] The pharmaceutical composition according to [8] or [9], wherein the disease associated with the reduced immune function caused by the formation of the PD-1/PD-L1 binding is cancer.

[11] The pharmaceutical composition according to [9] or [10], wherein the cancer is skin cancer including malignant melanoma, brain tumor including glioblastoma, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, breast cancer, prostate cancer, testicular cancer, uterine cancer, cervical cancer, ovarian cancer, osteosarcoma, chondrosarcoma, rhabdomyosarcoma, leiomyosarcoma, leukemia including adult T-cell leukemia, malignant lymphoma or multiple myeloma.

[12] The pharmaceutical composition according to [8] or [9], wherein the disease associated with the reduced immune function caused by the formation of PD-1/PD-L1 binding is infection.

[13] The pharmaceutical composition according to [9] or [12], wherein the infection is tuberculosis, Hepatitis B, Hepatitis C, Human Immunodeficiency Virus (HIV) infection, Human Papillomavirus (HPV) infection, Epstein-Barr virus (EBV) infection, Human cytomegalovirus (CMV) infection, Herpes simplex virus infection or Human T-cell leukemia virus type 1 (HTLV-1) infection.

[14] An inhibitor of immune checkpoint comprising the compound according to any of [1] to [6] or a pharmaceutically acceptable salt thereof.

[15] The inhibitor according to [14], wherein the immune checkpoint is PD-L1.

[16] An inhibitor of PD-L1 expression comprising the compound according to any of [1] to [6] or a pharmaceutically acceptable salt thereof.

[17] An inhibitor of reduced production of IL-2 comprising the compound according to any of [1] to [6] or a pharmaceutically acceptable salt thereof.

[18] A vaccine adjuvant comprising the compound according to any of [1] to [6] or a pharmaceutically acceptable salt thereof.

In addition, the present invention provides the following embodiments.

[19] A method of treating a disease associated with the reduced immune function caused by the formation of PD-1/PD-L1 binding, which comprises administering a therapeutically effective amount of the compound according to any of [1] to [6] or a pharmaceutically acceptable salt thereof to a patient in need thereof.

[20] The compound according to any of [1] to [6] or a pharmaceutically acceptable salt thereof for use in the treatment of a disease associated with the reduced immune function caused by the formation of PD-1/PD-L1 binding.

[21] Use of the compound according to any of [1] to [6] or a pharmaceutically acceptable salt thereof in the manufacture of an agent for treating a disease associated with the reduced immune function caused by the formation of PD-1/PD-L1 binding.

[22] A method of inhibiting the expression of an immune checkpoint molecule, which comprises administering a therapeutically effective amount of the compound according to any of [1] to [6] or a pharmaceutically acceptable salt thereof to a patient in need thereof.

[23] The method according to [22], wherein the immune checkpoint molecule is PD-L1.

[24] A method of inhibiting the reduced production of IL-2, which comprises administering a therapeutically effective amount of the compound according to any of [1] to [6] or a pharmaceutically acceptable salt thereof to a patient in need thereof.

[25] An enhancer of T-cell function comprising the compound according to any of [1] to [6] or a pharmaceutically acceptable salt thereof.

[26] A method of enhancing T-cell function, which comprises administering a therapeutically effective amount of the compound according to any of [1] to [6] or a pharmaceutically acceptable salt thereof to a patient in need thereof.

Effects of the Invention

The compound of the present invention has an inhibitory effect of PD-L1 expression and an inhibitory effect of reduced production of IL-2 and is useful as a novel agent for treating a disease associated with the reduced immune function caused by the formation of PD-1/PD-L1 binding, particularly cancer (e.g., skin cancer including malignant melanoma, brain tumor including glioblastoma, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, breast cancer, prostate cancer, testicular cancer, uterine cancer, cervical cancer, ovarian cancer, osteosarcoma, chondrosarcoma, rhabdomyosarcoma, leiomyosarcoma, leukemia including adult T-cell leukemia, malignant lymphoma, multiple myeloma) and infection (e.g., tuberculosis, Hepatitis B, Hepatitis C, Human Immunodeficiency Virus (HIV) infection, Human Papillomavirus (HPV) infection, Epstein-Barr virus (EBV) infection, Human cytomegalovirus (CMV) infection, Herpes simplex virus infection, or Human T-cell leukemia virus type 1 (HTLV-1) infection). Also, the compound of the present invention is useful as a vaccine adjuvant because it inhibits immune checkpoint molecules.

BRIEF DESCRIPTION OF THE DRAWINGS

FIG. 1 is a view analyzing the expression of PD-L1 or PD-1 on the surface of each cell.

DESCRIPTION OF EMBODIMENTS

Each term as used herein is explained below.

As used herein, the term "halogen" means fluorine, chlorine, bromine or iodine.

As used herein, the term "$C_{1-6}$ alkyl" means a linear or branched-chain saturated hydrocarbon having 1 to 6 carbon atoms. The "$C_{1-6}$ alkyl" may be optionally substituted with one or more groups defined in the present invention at any replaceable positions. Preferably, the "$C_{1-6}$ alkyl" may have 1 to 5, 1 to 4 or 1 to 3 carbon atoms. Examples thereof include methyl, ethyl, propyl, isopropyl, butyl, isobutyl, sec-butyl, tert-butyl, pentyl, isopentyl, neopentyl and hexyl, but are not limited thereto.

As used herein, the term "$C_{1-6}$ haloalkyl" means the above-mentioned alkyl group having 1 to 6 carbon atoms in which one or more hydrogen atoms are substituted with halogen atom(s). The number of substituted hydrogen atom may range from 1 to the total number of hydrogen atoms that can be present in the parent alkyl group. When multiple halogen atoms are present in the group, they may be same or different. Examples thereof include chloromethyl, trifluoromethyl and 2,2,2-trifluoroethyl, but are not limited thereto.

As used herein, the term "$C_{1-6}$ hydroxyalkyl" means the above-mentioned alkyl group having 1 to 6 carbon atoms in which one or more hydrogen atoms are substituted with hydroxy group(s). The number of substituted hydrogen atoms may range from one to the total number of hydrogen atoms that can be present in the parent alkyl group. Examples thereof include hydroxymethyl, 2-hydroxyethyl, 2-hydroxypropyl, 3-hydroxypropyl and 4-hydroxybutyl, but are not limited thereto.

As used herein, the term "$C_{1-6}$ alkoxy" means a group in which the above-mentioned alkyl group having 1 to 6 carbon atoms is attachable via oxygen atom. Examples thereof include methoxy, ethoxy, propoxy, isopropoxy, butyloxy, pentyloxy, isopentyloxy, neopentyloxy and hexyloxy, but are not limited thereto.

As used herein, the term "$C_{1-6}$ haloalkoxy" means the above-mentioned alkoxy group having 1 to 6 carbon atoms in which one or more hydrogen atoms are substituted with halogen atom(s). The number of substituted hydrogen atoms may range from 1 to the total number of hydrogen atoms that can be present in the parent alkyl group. When multiple halogen atoms are present in the group, they may be same or different. Examples thereof include chloromethoxy, trifluoromethoxy and 2,2,2-trifluoroethoxy, but are not limited thereto.

As used herein, the term "$C_{1-6}$ hydroxyalkoxy" means the above-mentioned alkoxy group having 1 to 6 carbon atoms in which one or more hydrogen atoms are substituted with hydroxy group(s). The number of substituted hydrogen atoms may range from one to the total number of hydrogen atoms that can be present in the parent alkyl group. Examples thereof include hydroxymethoxy, 2-hydroxyethoxy, 2-hydroxypropoxy, 3-hydroxypropoxy and 4-hydroxybutoxy, but are not limited thereto.

As used herein, the term "mono- or di-$C_{1-6}$ alkylamino" means an amino group in which one or two hydrogen atoms are substituted with the above-mentioned alkyl group having 1 to 6 carbon atoms. When an amino group is substituted with two alkyl groups, the alkyl groups may be same or different. Examples thereof include methylamino, ethylamino, dimethylamino and diethylamino, but are not limited thereto.

As used herein, the term "$C_{1-4}$ acyl" means a carbonyl (—C(=O)—) group which is linked to the above-mentioned alkyl group having 1 to 3 carbon atoms. Examples thereof include formyl, acetyl and propionyl, but are not limited thereto.

As used herein, the term "aryl" means a mono- or bi-cyclic aromatic hydrocarbon group having 6 or more carbon atoms in which one hydrogen atom attached to the aromatic ring is excluded. The "aryl" may be optionally substituted with one or more groups defined in the present invention at any replaceable positions. Examples thereof include phenyl, 1-naphtyl, 2-naphtyl and anthracenyl, but are not limited thereto.

As used herein, the term "heteroaryl" means a mono- or bi-cyclic aromatic heterocyclyl group in which at least one carbon atom in the ring is substituted with heteroatom(s) selected independently from the group consisting of nitrogen atom, oxygen atom and sulfur atom. The "heteroaryl" may be optionally substituted with one or more groups defined in the present invention at any replaceable positions. The preferred "heteroaryl" may be 3- to 10-membered heteroaryl, 3- to 6-membered heteroaryl and 5- to 6-membered heteroaryl. For example, the "5- to 6-membered heteroaryl" is a 5- to 6-membered monocyclic heterocyclyl group including at least one heteroatom selected from nitrogen atom, oxygen atom or sulfur atom. Examples thereof include thiophen, furan, pyrrole, imidazole, pyrazole, thiazole, oxazole, isothiazole, isoxazole, pyridine, pyrimidine, pyrazine, pyridazine, triazine, indole, purine, quinoline and isoquinolin, but are not limited thereto.

As used herein, the term "optionally substituted" means a case in which the position is not substituted (non-substituted) and a case in which it is substituted at a position which can be substituted. The term "non-substituted" means that all of the replaceable positions in a group are hydrogen atoms. When a group is substituted, the group may be substituted with two or more substituents, if possible, and the substituents may be same or different. Examples of the substituent include halogen, alkyl group, alkenyl group, alkynyl group, cycloalkyl group, haloalkyl group, hydroxyalkyl group, alkoxy group, haloalkoxy group, hydroxyalkoxy group, amino group, nitro group, cyano group, hydroxy group, carbamoyl group, carboxyl group, morpholinyl group, formyl group, acetyl group, mesyl group, benzoyl group and acylamino group.

$R^1$, $R^2$, m and n in the compound of the present invention represented by the formula (I) are preferably selected as follows, but the technical scope of the present invention is not limited to the scope of the compounds listed below.

$R^1$ and $R^2$ include halogen, hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro, amino, mono- or di-$C_{1-6}$ alkylamino, pentafluorosulfanyl, aryl and heteroaryl, wherein said aryl and heteroaryl may be optionally substituted with one group or the same or different two or more groups selected independently from the group consisting of halogen, hydroxy, cyano, nitro, amino, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, $C_{1-6}$ haloalkoxy and $C_{1-6}$ hydroxyalkoxy at any replaceable positions.

$R^1$ is preferably halogen, hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro or pentafluorosulfanyl, more preferably hydroxy, $C_{1-6}$ alkyl, $C_{1-6}$ alkoxy or nitro, furthermore preferably hydroxy, $C_{1-6}$ alkoxy or nitro, and most preferably hydroxy, methoxy or nitro.

$R^2$ is preferably halogen, hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro or pentafluorosulfanyl, more preferably halogen, $C_{1-6}$ alkyl, $C_{1-6}$ haloalkyl, $C_{1-6}$ alkoxy or pentafluorosulfanyl, furthermore preferably $C_{1-6}$ haloalkyl or pentafluorosulfanyl, and most preferably trifluoromethyl or pentafluorosulfanyl.

m and n are an integer of 0 to 5, preferably an integer of 1 to 4, more preferably an integer of 1 to 3, and most preferably an integer of 1 to 2.

Examples of the "pharmaceutically acceptable salt" of the compound of formula (I) include a salt with an inorganic acid, a salt with an organic acid. Examples of the salt with an inorganic acid include inorganic acid salts such as hydrochloride, hydrobromide, hydroiodide, nitrate, sulfate and phosphate. Examples of the salt with an organic acid include organic acid salts such as acetate, oxalate, fumarate, maleate, succinate, malate, citrate, tartrate, adipate, gluconate, glucoheptonate, glucuronate, terephthalate, methanesulfonate, alanine, lactate, hippurate, 1,2-ethanedisulfonate, isethionate, lactobionate, oleate, gallate, pamoate, polygalacturonate, stearate, tannate, trifluoromethanesulfonate, benzenesulfonate, p-toluenesulfonate, naphthalenesulfonate and sulfosalicylate.

The compound of the present invention may be present in the form of a hydrate and/or solvate, and the hydrate and/or solvate is also included in the compound of the present invention. Examples of the solvate include ethanol solvate.

Hereinafter, the method of preparing the compound of the present invention is illustrated with an example, but the invention is not limited thereto. The typical compound of the present invention represented by formula (I) can be prepared according to the following process:

Compound (1-3)

Compound (1-4)

wherein $R^1$ is $CF_3$ or $SF_5$, $R^2$ is OH or $NO_2$, and $R^3$ is H or $OCH_3$.

Compound (1-1) may be a commercially available product or be prepared according to known synthesis method.

Step 1: Preparation Process of Compound (1-2)

Compound (1-2) is prepared by reacting compound (1-1) with 4-chlorobenzotrifluoride or 4-fluorophenylsulfur pentafluoride in an appropriate solvent in the presence of a base.

Step 2: Preparation Process of Compound (1-3)

Compound (1-3) is prepared by reacting compound (1-2) with 1-(tert-butoxycarbonyl)-4-piperidine-carboxylic acid in an appropriate solvent in the presence of a base.

Step 3: Preparation Process of Compound (1-4) Compound (1-4) is prepared by reacting compound (1-3) with carboxylic acid A under an acidic (HCl) condition in an appropriate solvent.

As appropriate, the solvent to be used in each step of the above processes should be selected according to various factors such as the kinds of reaction and starting compound. Examples thereof include alcohols such as methanol, ethanol, and isopropanol; ketones such as acetone and methylketone; halogenated hydrocarbons such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as dimethylformamide (DMF) and N-methyl-2-pyrrolidone; sulfoxides such as dimethylsulfoxide (DMSO); and nitriles such as acetonitrile. These solvents may be used alone or in combination with two or more solvents.

As appropriate, the base to be used in each step of the above processes should be selected according to various factors such as the kinds of reaction and starting compound. Examples thereof include potassium carbonate, sodium carbonate, cesium carbonate, potassium tert-butoxide, sodium hydride, potassium hydroxide, sodium bis(trimethylsilyl) amide and lithium diisopropylamide, and these bases may be used alone or in combination with two or more bases.

Examples of the "cancer" as used herein include solid cancer, blood cancer and metastatic cancer, and the cancer type is not particularly limited.

Examples of the solid cancer include skin cancer (e.g., malignant melanoma), brain tumor (e.g., glioblastoma), lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, breast cancer, prostate cancer, testicular cancer, uterine cancer, cervical cancer, ovarian cancer, osteosarcoma, chondrosarcoma, rhabdomyosarcoma and leiomyosarcoma.

Examples of the blood cancer include multiple myeloma, malignant lymphoma (e.g., Non-Hodgkin lymphoma, Hodgkin lymphoma) and leukemia (e.g., adult T-cell leukemia, acute myelogenous leukemia and chronic myelogenous leukemia).

Examples of the metastatic cancer include metastatic lung cancer, metastatic gastric cancer, metastatic colorectal cancer, metastatic liver cancer, metastatic pancreatic cancer, metastatic renal cancer, metastatic adrenal cancer, metastatic esophageal cancer, metastatic bladder cancer, metastatic thyroid cancer, metastatic breast cancer, metastatic prostate cancer and metastatic uterine cancer.

Examples of the "infection" as used herein include bacterial infection and virus infection, and the pathogen is not particularly limited. Examples thereof include tuberculosis, Hepatitis B, Hepatitis C, Human Immunodeficiency Virus (HIV) infection, Human Papillomavirus infection, Epstein-Barr virus infection, cytomegalovirus infection, Herpes simplex virus infection and Human T-cell leukemia virus type 1 (HTLV-1) infection, but are not limited thereto.

As used herein, the term "inhibitor of immune checkpoint" means an agent that inhibits the function of one or more immune checkpoint molecules (e.g., PD-1 and PD-L1) or the formation of PD-1/PD-L1 binding, and then cancels the suppression of T-cells and activates the T-cells to produce an immunostimulatory effect. The immune checkpoint molecule is a protein for inhibiting the activation of killer T-cells and suppressing immunity to cancer cells or pathogens.

As used herein, the term "inhibitor of PD-L1 expression" means an agent that suppresses the expression of PD-L1 in cancer cells or antigen presenting cells, inhibits the formation of PD-1/PD-L1 binding, and then cancels the suppression of T-cells and activates the T-cells to produce an immunostimulatory effect on cancer cells or pathogens.

As used herein, the term "inhibitor of reduced production of IL-2" means an agent that inhibits the formation of PD-1/PD-L1 binding, inhibits the reduced production of IL-2, and then inhibits the apoptosis of T-cells and activates the T-cells to produce an immunostimulatory effect on cancer cells or pathogens.

As used herein, the term "treatment (treating)" means the treatment and/or improvement of a disease or disorder and the associated symptom in mammals, particularly in humans. Also, the term includes preventing, relieving or alleviating a disease associated with the reduced immune function caused by the formation of PD-1/PD-L1 binding. Examples of the treatment of cancer include completely removing cancer tumors, killing cancer cells, suppressing the proliferation of cancer cells, inhibiting recurrence of cancer, removing the symptom associated with cancer, relieving or alleviating the symptom associated with cancer, preventing or delaying the aggravation of cancer and the associated symptom, preventing or delaying the progression of cancer and the associated symptom, improving the quality of life for cancer patients, prolonging the survival of cancer patients, preventing or delaying the development of cancer and the associated symptom, and reducing the risk of developing cancer and the associated symptom. Also, examples of the treatment of infection include completely removing pathogens that cause infection, suppressing the proliferation of pathogens, inhibiting recurrence of infection, relieving or alleviating the symptom associated with infection, preventing or delaying the aggravation of the symptom associated with infection, and preventing or delaying the progression of the symptom associated with infection.

As used herein, the term "patient" means a human and an animal such as a dog, a cat and a horse. Among them, a human is preferable.

As used herein, the term "therapeutically acceptable amount" means an amount which can provide the treatment, improvement, prevention and/or relief of a disease associated with the reduced immune function caused by the formation of PD-1/PD-L1 binding and the associated symptom or an amount which can provide the prevention or delay of the progression of symptom associated with cancer, compared with untreated subjects. The term also includes, within its scope, an amount effective to promote normal physiological functions. On the use in the treatment, the therapeutically acceptable amount of the compound of the present invention may be construed as the administered amount of the compound ingredient. The effective dose of the compound of the present invention is generally the range of 0.001 to 1000 mg/kg (body weight) per day, but is not limited thereto.

The therapeutically effective amount includes the amount of the compound of the present invention alone, the amount of a combination of the plural compounds of the present invention, and/or the amount of the compound of the present invention in combination with other active ingredients useful for cancer treatment.

As used herein, the term "enhancement of T-cell function (enhancing T-cell function)" means that PD-1 expression in T-cells, PD-L1 expression in cancer cells and the reduced T-cell function caused by the formation of PD-1/PD-L1 binding are activated. Examples of enhancing T-cell function include increasing the production amount of cytokine (IL-2), accelerating the proliferation of T-cells, and cancellation and suppression of tolerance of T-cells in the suppressed state such as the anergy (unresponsive) state and the rest state (transferring T-cells from the suppressed state into the state into the state where the T-cells respond to stimulation from outside).

The pharmaceutical composition as well as inhibitor of immune checkpoint, inhibitor of PD-L1 expression, inhibitor of reduced production of IL-2, vaccine adjuvant and enhancer of T-cell function (hereinafter, referred to as "agent") of the present invention comprise the compound of the present invention as an active ingredient, and may further comprise other ingredients as long as they do not prevent the inhibitory effect of immune checkpoint molecules. Hence, the proportion of the compound of the present invention in the pharmaceutical composition or agent is not limited to specific ones. For example, the pharmaceutical composition or agent of the present invention may comprise 0.1% by weight or more, 0.5% by weight or more, or 1.0% by weight or more of the compound of the present invention. Also, the amount of the compound of the present invention may be the range of 0.1 to 90% by weight, 0.5 to 70% by weight or 1.0 to 60% by weight. Alternatively, the pharmaceutical composition or agent of the present invention may consist of only the compound of the present invention.

The pharmaceutical composition or agent of the present invention can be orally or parenterally (e.g., intravenously, topically, trans nasally, pulmonary and rectally) administered. The dosage form of the present invention can be optionally selected and prepared according to physical and health condition, etc. of a subject. For example, the compound of the present invention can be prepared as a dosage form for oral administration such as a tablet, a capsule, a granule, a powder, a solution and a syrup, or a dosage form for parenteral administration such as an injection, a dialysis agent, an inhalant, a suppository, eye drops, an ophthalmic ointment, ear drops, nasal drops, a topical agent, a spray, an ointment, a cream, a gel and a patch, according to a conventional method.

The pharmaceutical composition or agent of the present invention may comprise one or more pharmaceutically acceptable carriers such as an excipient (e.g., lactose, white soft sugar, D-mannitol and crystalline cellulose), a disintegrant (e.g., carmellose, carmellose sodium and low substituted hydroxypropyl cellulose), a binding agent (e.g., hydroxypropyl cellulose, hydroxypropylmethyl cellulose, povidone and crystalline cellulose), a lubricant (e.g., magnesium stearate, calcium stearate and talc), a solvent (e.g., water, ethanol and propylene glycol), a buffering agent (e.g., trisodium phosphate, sodium hydrogen phosphate and sodium dihydrogen phosphate), a suspending agent (e.g., gum arabic, tragacanth and carboxymethyl cellulose sodium), an emulsifier (e.g., glycerol fatty acid ester and sorbitan fatty acid ester).

The dosage of the compound of the present invention may be selected according to various factors such as a mode of administration, an age of a subject, a degree of a disease, a symptom, a dosage form. For example, the compound may be orally administered at a dose of 0.01 mg to 0.1 mg, 0.1 mg to 1 mg, 1 mg to 5 mg, 5 mg to 10 mg, 10 mg to 50 mg, 50 mg to 100 mg, 100 mg to 500 mg, 500 mg to 1 g, 1 g to 1.5 g, 1.5 g to 2 g, 2 g to 5 g or 5 g to 10 g per day. The daily dosage of the compound of the present invention may be administered in one or several portions.

EXAMPLES

Hereinafter, the present invention is illustrated in more detail with Reference Examples, Examples and Test Examples, but the present invention should not be limited thereto. The identification of each compound was performed by conventional methods such as nuclear magnetic resonance (NMR) spectroscopy and mass spectrometry.

The following abbreviations may be used herein for the sake of simplicity. The signs used in NMR are follows: s means singlet, d means doublet, dd means doublet of doublet, ddd means doublet of doublet of doublet, dt means doublet of triplet, t means triplet, td means triplet of doublet, q means quartet, m means multiplet, br means broad, brs means broad singlet, and J means coupling constant.

Reference Example 1

4-(4-(Trifluoromethyl)phenoxy)aniline p-Aminophenol (303 mg, 2.78 mmol), 4-chlorobenzotrifluoride (505 mg, 2.80 mmol) and potassium hydroxide (304 mg, 5.42 mmol) were dissolved in dimethyl sulfoxide (5 mL) and the solution was stirred at 100° C. for 12 hours. To the reaction solution was added water (10 mL), and then the mixture was extracted with ethyl acetate (10 mL) three times. The combined ethyl acetate layer was washed with water (20 mL) and brine (20 mL), dried over anhydrous sodium sulfate, and the solvent therein was removed in vacuo. The residue was purified by silica gel column chromatography (elution with hexane-ethyl acetate (7:3)) to provide 4-(4-(trifluoromethyl)phenoxy)aniline (181 mg, 0.715 mmol, 26%).

Reference Example 2

4-(4-(Pentafluorosulfanyl)phenoxy)aniline p-Aminophenol (189 mg, 1.78 mmol), 4-fluorophenylsulfur pentafluoride (258 mg, 1.16 mmol) and sodium hydride (60%, dispersed in liquid paraffin) (70 mg, 1.75 mmol) were dissolved in N,N-dimethylformamide (4 mL) and the solution was stirred at 100° C. for 18 hours. To the reaction solution was added water (10 mL), and then the mixture was extracted with ethyl acetate (10 mL) four times. The combined ethyl acetate layer was washed with water (20 mL) and brine (20 mL), dried over anhydrous sodium sulfate, and the solvent therein was removed in vacuo. The residue was purified by silica gel column chromatography (elution with hexane-ethyl acetate (3:1)) to provide 4-(4-(pentafluorosulfanyl)phenoxy)aniline (110 mg, 0.354 mmol, 30%).

Reference Example 3 tert-Butyl 3-((4-(4-(trifluoromethyl)phenoxy)phenyl) carbamoyl)piperidine-1-carboxylate 4-(4-(trifluoromethyl)phenoxy)aniline (95.0 mg, 0.375 mmol) was dissolved in dichloromethane (4 mL), 1-(tert-butoxycarbonyl)-4-piperidine-carboxylic acid (108 mg, 0.471 mmol), N,N-diisopropylethylamine (200 μL, 1.14 mmol) and (1-cyano-2-ethoxy-2-oxoethylideneaminooxy) dimethylamino-morpholino-carbenium hexafluorophosphate (220 mg, 0.514 mmol) were the added to the solution, and then the mixture was stirred at room temperature for 6 hours. To the reaction solution was added 0.5 M hydrochloric acid (10 mL), and then the mixture was extracted with ethyl acetate (10 mL) three times. The combined ethyl acetate layer was washed with saturated aqueous sodium hydrogen carbonate solution (20 mL) and brine (20 mL), dried over anhydrous sodium sulfate, and the solvent therein was removed in vacuo. The residue was purified by silica gel column chromatography (elution with hexane-ethyl acetate (3:1)) to provide tert-butyl 3-((4-(4-(trifluoromethyl)phenoxy) phenyl)carbamoyl)piperidine-1-carboxylate (134 mg, 0.289 mmol, 77%).

Reference Example 4 tert-Butyl 3-((4-(4-(pentafluorosulfanyl)phenoxy) phenyl) carbamoyl)piperidine-1-carboxylate 4-(4-(Pentafluorosulfanyl)phenoxy)aniline (70.1 mg, 0.225 mmol) was dissolved in dichloromethane (3 mL), 1-(tert-butoxycarbonyl)-4-piperidine-carboxylic acid (66.2 mg, 0.289 mmol), N,N-diisopropylethylamine (120 μL, 0.669 mmol) and (1-cyano-2-ethoxy-2-oxoethylideneaminooxy)dimethylamino-morpholino-carbenium hexafluorophosphate (141 mg, 0.330 mmol) were added to the solution, and then the mixture was stirred at room temperature for 10 hours. To the reaction solution was added 0.5 M hydrochloric acid (10 mL), and then the mixture was extracted with ethyl acetate (10 mL) three times. The combined ethyl acetate layer was washed with saturated aqueous sodium hydrogen carbonate solution (20 mL) and brine (20 mL), dried over anhydrous sodium sulfate, and the solvent therein was removed in vacuo. The residue was purified by silica gel column chromatography (elution with hexane-ethyl acetate (4:1)) to provide tert-butyl 3-((4-(4-(pentafluorosulfanyl) phenoxy) phenyl)carbamoyl)piperidine-1-carboxylate (61.0 mg, 0.117 mmol, 52%).

Example 1

1-(4-Hydroxybenzoyl)-N-(4-(4-(trifluoromethyl) phenoxy) phenyl)piperidine-3-carboxamide The compound of Reference Example 3 (30.2 mg, 0.065 mmol) was dissolved in hydrogen chloride-methanol reagent (5-10%) (2 mL) and the solution was stirred at room temperature for 4 hours. The reaction solution was removed in vacuo and the residue was dissolved in dichloromethane (2 mL), p-hydroxybenzoic acid (11.5 mg, 0.083 mmol), N,N-diisopropylethylamine (60 μL, 0.344 mmol) and (1-cyano-2-ethoxy-2-oxoethylideneaminooxy)dimethyl-amino-morpholino-carbenium hexafluorophosphate (38.5 mg, 0.090 mmol) were added to the solution, and then the mixture was stirred at room temperature for 4 hours. To the reaction solution was added 0.5 M hydrochloric acid (10 mL) and the mixture was extracted with ethyl acetate (10 mL) three times. The combined ethyl acetate layer was washed with saturated aqueous sodium hydrogen carbonate solution (20 mL) and brine (20 mL), dried over anhydrous sodium sulfate, and the solvent therein was removed in vacuo. The residue was purified by silica gel column chromatography (elution with chloroform-methanol (39:1)) to provide the title compound (16.1 mg, 0.033 mmol, 51%).

The product was analyzed by electron impact mass spectrometry (EIMS) and NMR. The results of EIMS and NMR are as follows.

$^1$H-NMR (600 MHz, CDCl$_3$) δ 9.14-9.32 (1H, br.s), 8.38-8.56 (1H, br.s), 7.56-7.66 (2H, br.s), 7.50 (2H, d, J=8.2 Hz), 7.25 (2H, d, J=7.6 Hz), 6.88-7.18 (4H, m), 6.68-6.83 (2H, br.s), 4.12-4.27 (1H, br.s), 3.59-3.78 (1H, br.s), 3.33-3.51 (1H, br.s), 2.61-2.79 (1H, br.s), 2.08-2.27 (1H, br.s), 1.92-2.08 (2H, br.s), 1.57-1.74 (1H, br.s), 1.43-1.57 (1H, br.s).

$^{13}$C-NMR (150 MHz, CDCl$_3$) δ 171.8, 171.3, 160.7, 158.8, 151.8, 134.7, 129.4 (2C), 127.1 (2C, q, $^3J_{C-F}$=3.8 Hz), 125.8, 124.7 (q, $^2J_{C-F}$=32.8 Hz), 124.2 (q, $^1J_{C-F}$=273.0 Hz), 121.9 (2C), 120.5 (2C), 117.4 (2C), 115.6 (2C), 49.1, 45.2, 43.5, 27.2, 24.7.

EIMS m/z (rel. int) 484 [M]$^+$ (100), 363 (42), 253 (35), 232 (30), 204 (93), 121 (91).

HREIMS m/z 484.1614 (Calculated value for C$_{26}$H$_{23}$O$_4$N$_2$F$_3$ 484.1608).

Example 2

1-(4-Nitrobenzoyl)-N-(4-(4-(trifluoromethyl)phenoxy)phenyl) piperidine-3-carboxamide The compound of Example 2 was synthesized according to a similar process to that of the compound of Example 1, except that p-nitrobenzoic acid was used in place of p-hydroxybenzoic acid.

The product was analyzed by electron impact mass spectrometry (EIMS) and NMR. The results of EIMS and NMR are as follows.

$^1$H-NMR (600 MHz, CDCl$_3$) δ 8.48-8.57 (1H, br.s), 8.28 (2H, d, J=8.4 Hz), 7.64 (2H, d, J=8.4 Hz), 7.53-7.62 (4H, m), 6.95-7.08 (4H, m), 4.14 (1H, br.d, J=14.1 Hz), 3.99 (1H, dd, J=14.1, 3.5 Hz), 3.34-3.51 (2H, m), 2.77-2.88 (1H, br.s), 2.23-2.37 (1H, br.s), 1.92-2.04 (1H, br.s), 1.62-1.73 (1H, br.s), 1.48-1.58 (1H, br.s).

$^{13}$C-NMR (150 MHz, CDCl$_3$) δ 171.8, 168.8, 160.6, 151.8, 148.6, 141.2, 134.6, 128.0 (2C), 127.0 (2C, q, $^3J_{C-F}$=3.9 Hz), 124.7 (q, $^2J_{C-F}$=33.1 Hz), 124.4 (q, $^1J_{C-F}$=270.8 Hz), 124.0 (2C), 121.9 (2C), 120.6 (2C), 117.4 (2C), 48.5, 44.4, 43.2, 27.2, 24.6.

EIMS m/z (rel. int) 513 [M]$^+$ (85), 261 (26), 253 (66), 233 (100), 150 (88).

HREIMS m/z 513.1507 (Calculated value for C$_{26}$H$_{22}$O$_5$N$_3$F$_3$ 513.1512).

Example 3

1-(4-Hydroxy-3-methoxybenzoyl)-N-(4-(4-(trifluoromethyl) phenoxy)phenyl)piperidine-3-carboxamide The compound of Example 3 was synthesized according to a similar process to that of the compound of Example 1, except that 4-hydroxy-3-methoxybenzoic acid was used in place of p-hydroxybenzoic acid.

The product was analyzed by electron impact mass spectrometry (EIMS) and NMR. The results of EIMS and NMR are as follows.

$^1$H-NMR (600 MHz, CDCl$_3$) δ 9.02-9.18 (1H, br.s), 7.66-7.82 (2H, br.s), 7.57 (2H, d, J=8.0 Hz), 6.91-7.08 (7H, m), 5.95-6.02 (1H, br.s), 4.06-4.22 (1H, br.s), 3.81-3.97 (1H, br.s), 3.83 (3H, s), 3.47-3.63 (1H, br.s), 2.61-2.75 (1H, br.s), 2.23-2.36 (1H, br.s), 1.86-1.98 (1H, br.s), 1.47-1.78 (3H, m).

$^{13}$C-NMR (150 MHz, CDCl$_3$) δ 171.8, 170.5, 160.6, 151.8, 149.6, 148.9, 134.6, 131.2, 127.0 (2C, q, $^3J_{C-F}$=3.9 Hz), 124.7 (q, $^2J_{C-F}$=33.1 Hz), 124.4 (q, $^1J_{C-F}$=270.8 Hz), 121.9 (2C), 120.9, 120.6 (2C), 117.4 (2C), 116.5, 114.7, 56.0, 49.2, 45.2, 43.3, 27.2, 24.7.

EIMS m/z (rel. int) 514 [M]$^+$ (61), 363 (24), 262 (25), 234 (96), 151 (100).

HREIMS m/z 514.1675 (Calculated value for C$_{27}$H$_{25}$O$_5$N$_2$F$_3$ 514.1716).

Example 4

1-(4-Hydroxybenzoyl)-N-(4-(4-pentafluorosulfanyl) phenoxy) phenyl)piperidine-3-carboxamide The compound of Reference Example 4 (42.2 mg, 0.080 mmol) was dissolved in hydrogen chloride-methanol reagent (5-10%) (2 mL) and the solution was stirred at room temperature for 6 hours. The reaction solution was removed in vacuo and the residue was dissolved in dichloromethane (2 mL), p-hydroxybenzoic acid (13.4 mg, 0.097 mmol), N,N-diisopropylethylamine (60 μL, 0.344 mmol) and (1-cyano-2-ethoxy-2-oxoethylideneaminooxy)dimethylamino-morpholino-carbenium hexafluorophosphate (45.0 mg, 0.105 mmol) were added to the solution, and then the mixture was stirred at room temperature for 3 hours. To the reaction solution was added 0.5 M hydrochloric acid (10 mL), and the mixture was extracted with ethyl acetate (10 mL) three times. The combined ethyl acetate layer was washed with saturated aqueous sodium hydrogen carbonate solution (20 mL) and brine (20 mL), dried over anhydrous sodium sulfate, and the solvent therein was removed in vacuo. The residue was purified by silica gel column chromatography (elution with chloroform-methanol (49:1)) to provide the title compound (22.7 mg, 0.042 mmol, 53%).

The product was analyzed by electron impact mass spectrometry (EIMS) and NMR. The results of EIMS and NMR are as follows.

$^1$H-NMR (600 MHz, CDCl$_3$) δ 9.23-9.34 (1H, br.s), 8.65-8.76 (1H, br.s), 7.68 (4H, m), 7.23 (2H, d, J=7.8 Hz), 6.98 (2H, d, J=8.0 Hz), 6.91 (2H, d, J=8.0 Hz), 6.76 (2H, d, J=7.8 Hz), 4.15-4.28 (1H, br.s), 3.72-3.88 (1H, br.s), 3.30-3.43 (1H, br.s), 2.68-2.82 (1H, br.s), 2.08-2.23 (1H, br.s), 1.87-2.02 (2H, br.s), 1.53-1.70 (1H, br.s), 1.40-1.53 (1H, br.s).

$^{13}$C-NMR (150 MHz, CDCl$_3$) δ 171.8, 171.3, 160.1, 158.9, 151.4, 148.0 (quint, $^2J_{C-F}$=17.8 Hz), 135.0, 129.4 (2C), 127.8 (2C, quint, $^3J_{C-F}$=4.4 Hz), 125.6, 122.0 (2C), 120.7 (2C), 116.8 (2C), 115.6 (2C), 49.1, 45.2, 43.5, 27.2, 24.8.

EIMS m/z (rel. int) 542 [M]$^+$ (42), 421 (20), 311 (20), 232 (30), 204 (100), 121 (93).

HREIMS m/z 542.1269 (Calculated value for C$_{25}$H$_{23}$O$_4$N$_2$F$_5$S 542.1299).

Example 5

1-(4-Nitrobenzoyl)-N-(4-(4-(pentafluorosulfanyl) phenoxy) phenyl)piperidine-3-carboxamide The compound of Example 5 was synthesized according to a similar process to that of the compound of Example 4, except that p-nitrobenzoic acid was used in place of p-hydroxybenzoic acid.

The product was analyzed by electron impact mass spectrometry (EIMS) and NMR. The results of EIMS and NMR are as follows.

$^1$H-NMR (600 MHz, CDCl$_3$) δ 8.48-8.57 (1H, br.s), 8.28 (2H, d, J=8.4 Hz), 7.56-7.68 (6H, m), 6.88-7.02 (2H, m), 6.73 (2H, d, J=7.7 Hz), 4.13 (1H, br.d, J=14.4 Hz), 3.94-4.03 (1H, m), 3.33-3.49 (2H, m), 2.78-2.88 (1H, br.s), 2.25-2.38 (1H, br.s), 1.92-2.03 (1H, br.s), 1.63-1.74 (1H, br.s), 1.48-1.58 (1H, br.s).

$^{13}$C-NMR (150 MHz, CDCl$_3$) δ 171.8, 168.9, 159.1, 151.3, 148.6, 148.1 (quint, $^2J_{C-F}$=17.2 Hz), 141.0, 135.0, 128.1 (2C), 127.8 (2C, quint, $^3J_{C-F}$=4.3 Hz), 124.0 (2C), 122.0 (2C), 120.5 (2C), 116.8 (2C), 48.7, 44.4, 43.2, 27.3, 24.8.

EIMS m/z (rel. int) 571 [M]$^+$ (100), 421 (10), 311 (42), 261 (20), 233 (64), 150 (48).

HREIMS m/z 571.1197 (Calculated value for C$_{25}$H$_{22}$O$_5$N$_3$F$_5$S 571.1200).

Example 6

1-(4-Hydroxy-3-methoxybenzoyl)-N-(4-(4-(pentafluorosulfanyl)phenoxy)phenyl)piperidine-3-carboxamide The compound of Example 6 was synthesized according to a similar process to that of the compound of Example 4, except that 4-hydroxy-3-methoxybenzoic acid was used in place of p-hydroxybenzoic acid.

The product was analyzed by electron impact mass spectrometry (EIMS) and NMR. The results of EIMS and NMR are as follows.

$^1$H-NMR (600 MHz, CDCl$_3$) δ 9.08-9.21 (1H, br.s), 7.60-7.83 (4H, m), 7.02-7.10 (5H, m), 6.92-7.02 (2H, m), 6.00-6.13 (1H, br.s), 4.03-4.15 (1H, br.s), 3.84-3.97 (1H, br.s), 3.83 (3H, s), 3.49-3.60 (1H, br.s), 2.71-2.80 (1H, br.s), 2.28-2.40 (1H, br.s), 1.88-2.00 (1H, br.s), 1.51-1.82 (3H, m).

$^{13}$C-NMR (150 MHz, CDCl$_3$) δ 171.8, 170.3, 159.0, 151.1, 149.8, 148.6, 148.0 (quint, $^2J_{C-F}$=17.2 Hz), 135.1, 131.0, 127.7 (2C, quint, $^3J_{C-F}$=4.1 Hz), 122.0 (2C), 121.3, 120.7 (2C), 116.7 (2C), 116.5, 114.4, 56.1, 49.0, 45.0, 43.6, 27.2, 24.6.

EIMS m/z (rel. int) 572 [M]$^+$ (100), 421 (42), 311 (19), 262 (26), 234 (94), 151 (88).

HREIMS m/z 572.1388 (Calculated value for C$_{26}$H$_{25}$O$_5$N$_2$F$_5$S 572.1404).

Comparative Example 1

N-(3-(4-Chlorophenoxy)phenyl)-1-(4-hydroxyphenylcarbonyl) piperidine-3-carboxamide The compound of Comparative Example 1 was prepared according to the following process. 3-(4-Chlorophenoxy) aniline (55 mg, 0.250 mmol) was dissolved in dichloromethane (3 mL), 1-(tert-butoxycarbonyl)piperidine-3-carboxylic acid (59 mg, 0.312 mmol), N,N-diisopropylethylamine (130 μL, 0.776 mmol) and (1-cyano-2-ethoxy-2-oxoethylideneaminooxy)dimethylamino-morpholino-carbenium (145 mg, 0.339 mmol) were added to the solution, and then the mixture was stirred at room temperature for 16 hours. To the reaction solution was added 0.3 M hydrochloric acid (20 mL), and the mixture was extracted with ethyl acetate (20 mL) three times. The combined ethyl acetate layer was washed with saturated aqueous sodium hydrogen carbonate solution (40 mL) and brine (40 mL), dried over anhydrous sodium sulfate, and the solvent therein was removed in vacuo. The residue was purified by silica gel column chromatography (elution with hexane-ethyl acetate (3:7)) to provide tert-butyl 3-(3-(4-chlorophenoxy)phenylamino)-3-oxopropylcarbamate (61 mg, 0.155 mmol, 62%).

tert-Butyl 3-(3-(4-chlorophenoxy)phenylamino)-3-oxopropylcarbamate (53 mg, 0.135 mmol) was methanol (1.5 mL), hydrochloric acid-methanol reagent (5-10%) (1.5 mL) was added to the solution, and then the mixture was stirred at room temperature for 4 hours. The reaction solution was removed in vacuo and the residue was dissolved in dichloromethane (3 mL). 4-(Methoxymethoxy)benzoic acid (32 mg, 0.175 mmol), N,N-diisopropylethylamine (100 μL, 0.574 mmol) and (1-cyano-2-ethoxy-2-oxoethylideneaminooxy)dimethylamino-morpholino-carbenium (90 mg, 0.210 mmol) were added to the solution, and then the mixture was stirred at room temperature for 12 hours. To the reaction solution was added 0.3 M hydrochloric acid (20 mL), and the mixture was extracted with ethyl acetate (20 mL) three times. The combined ethyl acetate layer was washed with saturated aqueous sodium hydrogen carbonate solution (40 mL) and brine (40 mL), dried over anhydrous sodium sulfate, and the solvent therein was removed in vacuo. The residue was purified by silica gel column chromatography (elution with chloroform-methanol (39:1)) to provide N-(3-(3-(4-chlorophenoxy)phenylamino)-3-oxopropyl)-4-(methoxymethoxy)benzamide (38 mg, 0.082 mmol, 61% (2 steps)).

N-(3-(3-(4-Chlorophenoxy)phenylamino)-3-oxypropyl)-4-(methoxymethoxy)benzamide (28 mg, 0.063 mmol) was dissolved in methanol (1 mL), hydrochloric acid-methanol reagent (5-10%) (1 mL) was added to the solution, and then the mixture was stirred at room temperature for 5 hours. The reaction solution was removed in vacuo and the residue was purified by silica gel column chromatography (elution with chloroform-methanol (19:1)) to provide the compound of Comparative Example 1 (9 mg, 0.022 mmol, 35%).

Test Example 1: Evaluation of Inhibitory Effect of Luciferase Expression Under Control of PD-L1 Promoter A reporter vector, pPD-L1luc obtained by the insertion of a human PD-L1 promoter sequence (−2097 to 51) into the multiple cloning site of pGL-3 vector basic (Promega) expresses luciferase under the control of PD-L1 promoter when transfected into animal cells. The pPD-L1luc was transfected into a human non-small cell lung cancer-derived cell line A549 together with pPUR (Clontech) that expresses a puromycin resistance gene (puromycin-N-acetyl-transferase gene), and then cells expressing luciferase which could grow in a puromycin-supplemented medium were selected. The selected cells were named "A549/PD-L1luc cells" and used for luciferase assay as described below.

A test compound was added into a culture liquid containing A549/PD-L1luc cells to observe the influence of the test compound on the amount of luciferase expressed in the cells. Here, it can be considered that when the test compound has a cell cytotoxicity or cell growth inhibitory effect, the total expression level of luciferase is recued due to a reduction in the number of living cells that depends on the concentration of the test compound, and thus the inhibitory effect of luciferase expression under the control of PD-L1 promoter of the test compound cannot be properly evaluated. Hence, the total protein amount of the cells cultured with the addition of the test compound was measured using BCA Protein Assay Kit (Thermo Scientific), and the total protein amount measured was used as an index of the number of cells.

(1-1) Luciferase Assay

A549/PD-L1luc cells were suspended in DMEM containing 10% fetal calf serum (FCS) and 1% penicillin/streptomycin (P/S) (hereinafter, referred to as "DMEM medium") at $3\times10^4$ cells/mL to obtain a cell suspension, and the cell suspension was dispensed into each well of a 96-well plate in an amount of 100 μL. In order to perform the assay in triplicate, 3 wells were prepared for control group, and 3 wells were prepared for test compound-treated groups at each concentration. After the dispensation, the 96-well plate was incubated in a $CO_2$ incubator (at 37° C. and 5% $CO_2$) for 24±4 hours.

Each compound of Examples 1 to 6 and Comparative Example 1 was dissolved in dimethylsulfoxide (DMSO) to obtain 50 mmol/L of a compound solution, and the compound solution was stored at −80° C. The compound solution was diluted with DMSO in 2-fold dilution series (usually, in the range of 0.04 mmol/L to 10 mmol/L) to prepare test compound solutions whose concentration varied by two fold for luciferase assay.

Each solution of only DMSO (control) and the diluted test compound (sample) was dispensed into each well containing the cell suspension in an amount of 0.5 μL (200-fold dilution). The solution in each well was mixed with a vortex mixer, and then the 96-well plate was incubated in a $CO_2$ incubator (at 37° C. and 5% $CO_2$) for 48±4 hours. Luciferase Assay Substrate (hereinafter, referred to as "LAS") supplied in Luciferase Assay Systems (Promega: Cat #E1500) was dissolved in Luciferase Assay Buffer (LAB) to prepare a luciferase reagent. 5× Cell Culture Lysis Reagent (hereinafter, referred to as "CCLR") was diluted by 5 times with water to prepare 1×CCLR.

After the incubation for 48±4 hours, the medium in each well was completely removed, and 1×CCLR was dispensed into each well in an amount of 50 μL. The plate was allowed to stand at room temperature for 30 minutes, and then 1×CCLR in each well was used as an assay sample for luciferase and total protein amount. The luciferase reagent (100 µL) was placed in a tube for chemiluminescence measurement assay, and the assay sample (20 µL) was added into the tube and mixed with the luciferase reagent to measure chemiluminescence (Relative Luminescence Intensity: RLU) using GloMax 20/20 (Promega).

(1-2) Measurement of Total Protein Amount in Cells

The above-mentioned assay sample (10 µL) was diluted by 10 times with water (90 µL). Each calibration curve sample was prepared by diluting the BSA solution with water as described in Table 1.

TABLE 1

| Vial | Water (µL) | Type and Amount of BSA solution added | Protein concentration (ng/mL) |
|---|---|---|---|
| — | — | — | 2000 |
| I | 140 µL | 22000 ng/mL BSA (20 µL) | 250 |
| II | 80 µL | Vial I (80 µL) | 125 |
| III | 90 µL | Vial II (60 µL) | 50 |
| IV | 80 µL | Vial III (80 µL) | 25 |
| V | 80 µL | Vial IV (20 µL) | 5 |
| VI | 80 µL | — | 0 |

BCA reagent A and BCA reagent B (50:1) supplied in a kit for protein assay were mixed to prepare Working Reagent. Each of the calibration curve samples (Vials I to VI) and the 10-fold diluted assay samples was dispensed into each well of a 96-well plate in an amount of 25 µL, respectively. The sample for the control group was dispensed into 2 wells in an amount of 25 µL, and each of the samples for the test compound-treated groups at each concentration was dispensed into 2 wells in an amount of 25 µL.

Working Reagent was added into each well containing the calibration curve sample or the assay sample in an amount of 200 µL, and the solution in each well was mixed with a vortex mixer for 30 seconds. After warming at 60° C. for 30 minutes, the plate was allowed to stand at room temperature for 15 minutes. The absorbance values (550 nm) were then measured with a microplate reader (Bio-Rad; Benchmark or Thermo Scientific; Varioskan Flash).

The regression line was determined from the absorbance values of the calibration curve samples by the method of least squares to calculate the total protein concentration of the diluted sample in each well. In addition, the total protein concentration was multiplied by the dilution factor (10) to calculate the total protein concentration of each sample.

(1-3) Calculation of 50% Expression Inhibition Concentration of PD-L1luc Activity ($IC_{50}$) The RLU values of the control and the samples at each concentration calculated in luciferase assay were input into an Excel file, and the percentages of the RLU values of the samples at each concentration to the average RLU value of the control samples were calculated.

In addition, the total protein concentrations of the control and the samples at each concentration calculated in the measurement of the total protein amount in cells were input into an Excel file, and the percentages of the total protein concentrations of the samples at each concentration to the average total protein concentration of the control samples were calculated.

Then, the percentage calculated from the RLU value of each sample was divided by that of the total protein concentration of the corresponding sample to calculate the percentage value calculated from the RLU value corrected by the protein amount. The regression line was determined from each corrected value by the method of least squares to calculate 50% inhibition value of luciferase expression ($IC_{50}$ value).

The calculated $IC_{50}$ values of each compound are shown in Table 2.

TABLE 2

| | $IC_{50}$ (µmol/L) |
|---|---|
| Example 1 | 1.3 |
| Example 2 | 1.3 |
| Example 3 | 0.61 |
| Example 4 | 1.2 |
| Example 5 | 0.62 |
| Example 6 | 0.61 |
| Comparative Example 1 | 14.1 |

The compounds of Examples 1 to 6 and Comparative Example 1 were evaluated in luciferase expression inhibitory test. As a result, it was observed that the compound of the present invention inhibited luciferase expression under the control of PD-L1 promoter.

Test Example 2: Evaluation of Inhibitory Effect of PD-L1 Expression by Cell Staining with Fluorescent Antibody-Labelled Anti-PD-L1 Antibody The inhibitory effects of each compound of Examples 1 to 6 on the PD-L1 expression were evaluated according to the following procedures.

(2-1) PD-L1 Expression Inhibition Assay (1) Acute monocytic leukemia cell-derived THP-1 cells were suspended in RPMI medium containing 10% FCS and 1% P/S (hereinafter, referred to as "RPMI medium") at $5 \times 10^5$ cells/mL to obtain a cell suspension, and the cell suspension was dispensed into each well of a 6 well-plate in an amount of 3 mL. In order to activate the THP-1 cells and express PD-L1 in the cells, IFN-γ (PEPROTECH, Cat. No. 300-02-100UG, >2e+7 U/mg) was added into each well at a concentration of 25 ng/mL (>500 U/mL). 50 mmol/L of the test compound solution was diluted with the medium (usually, in the range of 0.025 mmol/L to 1 mmol/L), and the diluted solution was added into each well in an amount of 60 µL. The plate was incubated in a $CO_2$ incubator (at 37° C. and 5% $CO_2$) for 24±2 hours. In the control group, only DMSO was added in place of the test compound.

(2) A part of the prepared cell culture liquid was collected and the number of cells therein was counted using a cell counter (BIORAD TC-20). The cell culture liquid was centrifuged at 300×g for 5 minutes and the supernatant of the cell culture liquid was removed. The cells were suspended in calcium and magnesium free phosphate buffered saline (PBS−) containing 1% bovine serum albumin (BSA) at a cell concentration of 1 to $2 \times 10^7$ cells/mL to prepare a cell suspension.

(3) Each cell suspension prepared in the above step (2) were added into a 5 mL tube in an amount of 25 µL. 2 µL of 2% normal mouse serum/PBS− was added into tubes, and the tubes were gently pipetted. The tubes were then allowed to stand at room temperature for 15 minutes.

(4) Anti-CD274-PC7 antibody (BECKMAN COULTER, Cat. No. A78884) or mouse IgG1-PC7 antibody (BECKMAN COULTER, 737662) as control was added in each tube in an amount of 10 µL, and the tubes were gently stirred. The tubes were then allowed to stand in the dark on an ice bath for 30 minutes.

(5) Foxp3/Transcription Factor Fix/Perm Concentrate (4×) (Cat. No. TNB-1020-L050) (A solution) supplied in FOXP3/Transcription Factor Staining kit (TONBO biosciences) was diluted in Foxp3/Transcription Factor Fix/Perm Diluent (1×) (Cat. No. TNB-1022-L160) (A dilution solution) to prepare a 1×A solution.

(6) The 1×A solution was added into each tube in an amount of 1 mL, and the tubes were gently pipetted and stirred. The tubes were then allowed to stand in the dark at room temperature for 30 minutes and centrifuged at 300×g for 5 minutes, and then the supernatants therein were removed.

(7) 2 mL of 1% BSA/PBS− was added into each tube and the tubes were gently stirred and centrifuged at 300×g for 5 minutes, and then the supernatants therein were removed.

(8) The cells therein were suspended in 0.5 mL of 1% BSA/PBS- and measured with a flow cytometer (Sony: Cell Sorter SH800) within 2 hours. The results were analyzed with a software, FlowJo (Tree Star Inc.). The mean peak fluorescence intensity (MFI) of PD-L1 and mean peak fluorescence intensity of IgG1 were calculated from histograms of the measured fluorescence intensity and number of cells, and the mean fluorescence intensity of IgG1 was subtracted from that of PD-L1 to calculate the subMFI. The experiments were performed in n=2.

(2-2) Calculation of 50% Expression Inhibition Concentration ($IC_{50}$) of PD-L1luc Activity The subMFI values of the control cells calculated by the FlowJo analysis and the cells cultured with the addition of the test compounds at each concentration (test cells) were input into an Excel file, and the percentages of the subMFI values of the test cells at each concentration to the average subMFI value of control cells were calculated. The regression line was determined from the percentages of the subMFI values of the test cells at each concentration by the method of least squares to calculate the 50% PD-L1 expression inhibition concentration ($IC_{50}$ value) of each compound.

The calculated $IC_{50}$ values of each compound are shown in Table 3.

TABLE 3

| | $IC_{50}$ (μmol/L) |
|---|---|
| Example 1 | 1.9 |
| Example 2 | 1.2 |
| Example 3 | 0.93 |
| Example 4 | 1.2 |
| Example 5 | 0.67 |
| Example 6 | 0.83 |

The compounds of Examples 1-6 were evaluated in the THP-1 cells stained with anti-PD-L1 antibody. As a result, it was confirmed that the compound of the present invention had an inhibitory effect of PD-L1 expression.

Test Example 3: Evaluation of Inhibitory Effect of the Compound of the Present Invention on Apoptosis of T-Cells Caused by the Formation of PD-1/PD-L1 Binding It was demonstrated from the results of Test Examples 1 and 2 that the compound of the present invention had the inhibitory effect of PD-L1 expression. As a result, it was evaluated whether the apoptosis of T-cells caused by the formation of PD-1/PD-L1 binding could be inhibited by the inhibitory effect of PD-L1 expression of the compound of the present invention.

The supernatants of each culture liquid containing A549 cells expressing PD-L1 pre-cultured with the addition of IFN-γ or human acute T-cell leukemia cell-derived Jurkat cells expressing PD-1 pre-cultured with the addition of Phorbol 12-myristate 13-Acetate (hereinafter, referred to as "PMA": Sigma Cat #1585) and phytohemagglutinin-L (hereinafter, referred to as "PHA-L": Roche Cat #11249738001) were removed, the culture liquids were co-cultured in new medium. The Caspase 3/7 activity of the co-cultured Jurkat cells was measured, and the measured activity was used as an index of apoptosis. Each test compound was added into the A549 cell culture liquid during the pre-culture.

(3-1) Caspase 3/7 Assay

[Day 1]

(1) A549 cells were suspended in DMEM medium at $1 \times 10^5$ cells/mL to prepare an A549 cell suspension, and the A549 cell suspension was dispensed into each well a 6 well plate in an amount of 3 mL.

(2) Separately, Jurkat cells were suspended in RPMI medium at $3 \times 10^5$ cells/mL to prepare a Jurkat cell suspension, and the Jurkat cell suspension was dispensed into a T25 flask in an amount of 5 mL.

(3) The 6-well plate of the above step (1) and the T25 flask of the above step (2) were incubated together in a $CO_2$ incubator (at 37° C. and 5% $CO_2$) for 24±2 hours.

[Day 2]

(1) To 3 mL of the A549 cell culture liquid were added IFN-γ (25 ng/mL) and a test compound, and the cell culture liquid was continuously cultured. The 50 mmol/L solution of the test compound in DMSO was diluted to 100 times with DMEM medium, and then the diluted solution was added as test compound group in an amount of 3 μL, 6 μL or 12 μL (final concentration: 0.5 μmol/L, 1.0 μmol/L or 2 μmol/L). In the control group, DMSO diluted to 100 times with DMEM medium was added in an amount of 12 μL.

(2) Separately, to the Jurkat cell culture liquid were added PMA (final concentration: 12.5 ng/mL) and PHA (final concentration: 250 ng/mL), and the cell culture liquid was continuously cultured.

[Day 3]

The cell culture liquids were observed.

[Day 4]

Cells were separated from A549 cell culture liquid with Cell Dissociation Solution Non-enzymatic (Sigma Cat No. C5914-100ML), and the cell culture liquid was centrifuged at 300×g for 5 minutes and the supernatant thereof was removed, and then the cells were suspended in RPMI medium at $4 \times 10^5$ cells/mL to prepare an A549 cell suspension.

The Jurkat cell culture liquid was centrifuged at 300×g for 5 minutes and the supernatant thereof was removed, and then the cells therein were suspended in RPMI medium at $4 \times 10^4$ cells/mL to prepare a Jurkat cell suspension.

0.25 mL of the prepared A549 cell suspension and 0.25 mL of the prepared Jurkat cell suspension (the ratio of the number of the cells is 10:1) were added into each well in a 24-well plate. 0.25 mL of A549 cells and 0.25 mL of RPMI medium were mixed and the mixture was cultured at 37° C. and 5% $CO_2$ to prepare an A549 blank containing only A549 cells which is not co-cultured with Jurkat cells. The PD-L1 expression in A549 cells after 2 days from IFN-γ treatment and the PD-1 expression in Jurkat cells stimulated with PMA and PHA were confirmed by staining the cells with anti-CD274-PC7 antibody (PD-L1) or anti-CD279-FITC antibody (PD-1, eBioscience Cat No. 11-9969-42) in a similar procedure to that of Test Example 2 and measuring the stained cells with a flow cytometer.

The cells were cultured under the following 6 conditions.

(IF−Comp−): Co-culture of A549 cells pre-cultured without the addition of IFN-γ and the test compound as well as Jurkat cells (IF+Comp−): Co-culture of A549 cells pre-cultured with the addition of IFN-γ and no test compound as well as Jurkat cells (IF+Comp+): Co-culture of A549 cells pre-cultured with the addition of IFN-γ and the test compound as well as Jurkat cells (A:IF−Comp−): Culture of only Co-culture of A549 cells pre-cultured without the addition of IFN-γ and the test compound (A:IF+Comp−): Culture of only A549 cells pre-cultured with the addition of IFN-γ and no test compound (A:IF+Comp+): Culture of only A549 cells pre-cultured with the addition of IFN-γ and the test compound

[Day 5]

The culture liquid (containing Jurkat cells which are suspension cells but not A549 cells which are adherent cells) was collected from each well and the collected culture liquid was used as the sample for measuring Caspase 3/7 using Caspase-Glo® 3/7 Assay Systems.

(3-2) Chemiluminescence Measurement (1) Preparation of Luciferase Reagent

Caspase-Glo® Buffer and Caspase-Glo® substrate supplied in Caspase-Glo® 3/7 Assay Systems (Promega, G8091) were returned to room temperature. 2.5 mL of Caspase-Glo® Buffer was added into the vial containing Caspase-Glo® substrate and mixed to prepare a luciferase reagent.

(2) Fluorescence Measurement

25 µL of the sample collected for measuring Caspase 3/7 activity and 25 µL of the luciferase reagent prepared in the above step (1) were mixed and incubated at room temperature for 1 hour, and then the chemiluminescence of the sample was measured using GloMax20/20 (Promega).

(3-3) Calculation of 50% Expression Inhibition Concentration ($IC_{50}$) of Caspase3/7 Activity Each value was calculated from the obtained Luminescence (CPS) to calculate the Caspase 3/7 activity inhibition ratio of each test compound according to the following formula:

$$\text{Capase 3/7 activity inhibition ratio (\%)} = 100 \times \left(1 - \frac{sub(IF + Comp +) - sub(IF - Comp -)}{sub(IF + Comp -) - sub(IF - Comp -)}\right)$$

wherein:
sub(IF+Comp+)=(IF+Comp+)−(A:IF+Comp+),
sub(IF+Comp−)=(IF+Comp−)−(A:IF+Comp−), and
sub(IF−Comp−)=(IF−Comp−)−(A:IF−Comp−).

Each concentration and Caspase 3/7 activity inhibition ratio of the test compounds were input into an Excel file, and the regression line was determined by the method of least squares to calculate the 50% expression inhibition concentration ($IC_{50}$ value) of each compound.

Figure 1A:
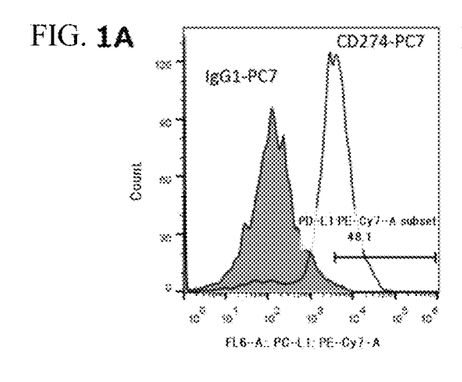
FIG. 1A is a view analyzing the expression of CD274 (PD-L1) on the surface of A549 cells after adding IFN-γ and culturing for 2 days.
Figure 1B:
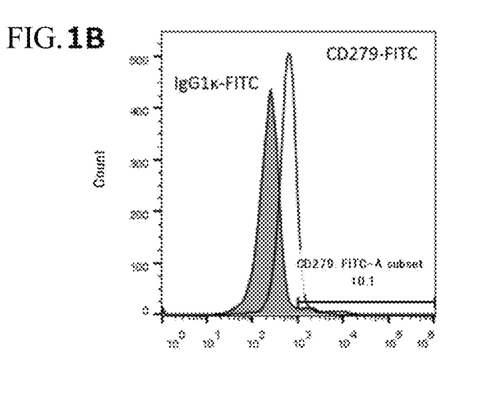
FIG. 1B is a view analyzing the expression of CD279 (PD-1) on the surface of Jurkat cells after adding PMA/PHA and culturing for 2 days.

The FCM analysis results (histgrams) of the A549 cells stained with anti-CD274-PC7 antibody or IgG1-PC7 antibody (isotype control) (after 2 days from treatment) and the Jurkat cells stained with anti-CD279-FITC antibody or IgG1κ-FITC antibody are shown in FIG. 1A and FIG. 1B.

Figure 2:
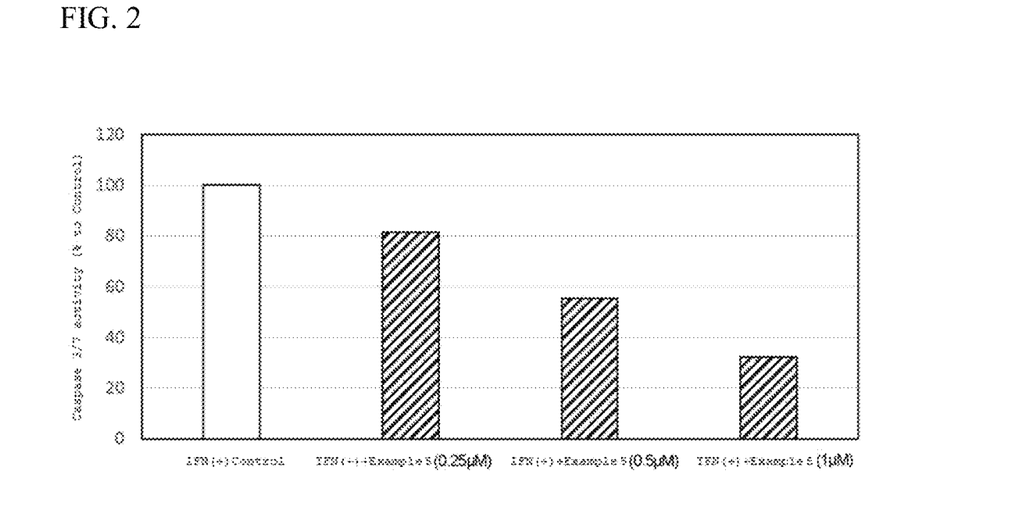
FIG. 2 is a view showing the inhibitory effect of the compound of Example 5 on apoptosis (Caspase 3/7 activity) of Jurkat cells after PD-1/PD-L1 binding is formed. It shows the ratio of each Caspase 3/7 activity of the compound of Example 5 (0.25 μM, 0.5 μM and 1 μM) to the Caspase 3/7 activity of control defined as 100%, in Jurkat cells.

In addition, the $IC_{50}$ values of the compounds of Examples 2, 3, 5 and 6 are shown in Table 4, and the Caspase 3/7 activities of the compound of Example 5 at each concentration to the Caspase 3/7 activity of the control (DMSO) defined as 100% are shown in Table 5 and FIG. 2.

Also, in order to confirm that the apoptosis due to the co-culture of A549 cells and Jurkat cells is caused by the formation of PD-1/PD-L1 binding, the PMA/PHA-treated Jurkat cells before co-culturing with the IFN-γ-treated A549 cells were preliminarily treated with anti-PD-1 antibody (R&D. AF1086; 10 mg/mL), and then the treated Jurkat cells and A549 cells were co-cultured for 3 hours to measure the Caspase 3/7 activity of the co-cultured Jurkat cells. The Caspase 3/7 activity of the anti-PD-1 antibody is also shown in Table 5.

TABLE 4

| Example No. | $IC_{50}$ (µmol/L) |
|---|---|
| 2 | 1.1 |
| 3 | 0.87 |
| 5 | 0.52 |
| 6 | 0.74 |

TABLE 5

| | Caspase 3/7 activity (%) |
|---|---|
| Control (DMSO) | 100 |
| Example 5 (0.25 µM) | 81.5 |
| Example 5 (0.5 µM) | 55.3 |
| Example 5 (1 µM) | 32.1 |
| Anti-PD-1 antibody (DMSO) | 13.5 |

From the above results, it was shown that the Caspase 3/7 activity was greatly reduced by the treatment with anti-PD-1 antibody in a pre-confirmed amount that can almost inhibit the formation of PD-1/PD-L1 binding. That is, it was shown that the Caspase 3/7 activity could be inhibited when the formation of PD-1/PD-L1 binding is inhibited, and it was demonstrated that the apoptosis induction due to the co-culture of A549 cells and Jurkat cells was caused by the formation of PD-1/PD-L1 binding. In addition, it was shown that the compound of the present invention could inhibit the apoptosis of Jurkat cells caused by the formation of PD-1/PD-L1 binding. As a result, it is found that the compound of the present invention has an inhibitory effect of apoptosis (activation of Caspase 3/7) of T-cells caused by the formation of PD-1/PD-L1 binding.

Test Example 4: Evaluation of Inhibitory Effect of the Compound of the Present Invention on the Reduced Production Amount of IL-2 in T-Cells Caused by the Formation of PD-1/PD-L1 Binding It was evaluated whether the reduced production amount of IL-2 in T-cells caused by the formation of PD-1/PD-L1 binding could be suppressed by the inhibitory effect of PD-L1 expression of the compound of the present invention.

The pIL-2luc obtained by the insertion of a human IL-2 promoter sequence (−945 to 53) into the multiple cloning site of pGL-3 vector basic (Promega) was preliminarily transfected into Jurkat cells. PMA and PHA-L were added into the Jurkat cells and the cells were pre-cultured. Simultaneously, IFN-γ was added into A549 cells and the cells were pre-cultured. The supernatants of each culture liquid at the time of the pre-culture of each cell were removed, the culture liquids were co-cultured in new medium. The luciferase activity of the co-cultured Jurkat cells was measured. Each test compound was added into the A549 cell culture liquid during the pre-culture.

[Day 1]

A549 cells were suspended in DMEM medium at a concentration of 3×10$^5$ cells/mL to prepare a suspension, and the suspension was dispensed into a T25 flask in an amount of 5 mL and cultured Separately, 5 µg of pIL-2luc DNA and 15 µL of TransIT-Jurkat reagent (Takara Bio: Cat #V2124) were added into 500 µL of serum-free medium, and the medium was allowed to stand at room temperature for 15 minutes. The total amount of the medium was added into Jurkat cells (3×10$^5$ cells/5 mL, RPMI medium/T25 flask).

[Day 2]

To 5 mL of the A549 cell culture liquid were added IFN-γ (25 ng/mL) and the compound of Example 5, and the culture liquid was continuously cultured. The 50 mmol/L solution of Compound 5 in DMSO was diluted to 100 times with DMEM medium, and then the diluted solution was added in an amount of 5 µL or 10 µL (final concentration: 0.5 µmol/L or 1.0 µmol/L). In the control group, DMSO diluted to 100 times with DMEM medium was added in an amount of 10 µL.

[Day 3]

Cells were separated from the A549 cell culture liquid with HyQTase, and the cell culture liquid was centrifuged at 300×g for 5 minutes and the supernatant thereof was removed, and then the cells were suspended in RPMI medium at a concentration of 4×10$^6$ cells/mL to prepare an A549 cell suspension.

The Jurkat cell culture liquid was centrifuged at 300×g for 5 minutes and the supernatant thereof was removed, and then the cells were suspended in RPMI medium at a concentration of 4×10$^5$ cells/mL to prepare a Jurkat cell suspension.

1 mL of the prepared A549 cell suspension and 1 mL of the prepared Jurkat cell suspension were added into each well in a 6-well plate (the ratio of the number of the cells is 10:1, the culture condition is at 37° C. and 5% CO$_2$).

[Day 4]

The supernatant of the culture liquid containing Jurkat cells was collected, and the culture liquid was centrifuged at 3000 rpm for 5 minutes. The collected supernatant was removed, 100 µL of Lysis buffer (1×CCLR prepared by diluting 5×CCLR with water) was added into a pellet and allowed to stand at room temperature for 15 minutes to prepare an assay sample.

LAS in Luciferase Assay System was dissolved in LAB to prepare a luciferase reagent. 10 µL of the sample was mixed with 50 µL of the luciferase reagent, and the chemiluminescence (Relative Luminescence Intensity: RLU) of the sample was measured using GloMax20/20 (Promega).

Figure 3:
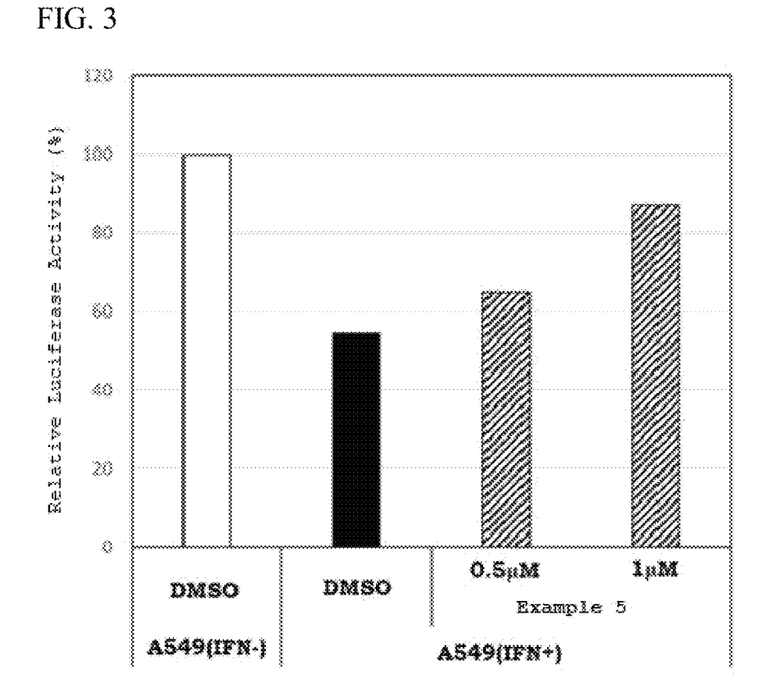
FIG. 3 is a view showing the inhibitory effect of the compound (Example 5) on the reduced production of IL-2 caused by the formation of PD-1/PD-L1 binding. It shows the ratio of each luciferase activity of control (DMSO) and the compound of Example 5 (0.5 μM and 1 μM) in A549 cells (with the addition of IFN-γ) to the luciferase activity of control (DMSO) in A549 cells (without the addition of IFN-γ) defined as 100%.

Each luciferase activity under the control of IL-2 promoter (hereinafter, referred to as "IL-2luc activity") in control (DMSO) and the compound of Example 5 at each concentration with the addition of IFN-γ to the IL-2luc activity in control (DMSO) without the addition of IFN-γ defined as 100% are shown in Table 6 and FIG. 3.

TABLE 6

|  | IL-2luc activity (%) |
|---|---|
| IFN-γ(−) | |
| Control (DMSO) | 100 |
| IFN-γ(+) | |
| Control (DMSO) | 54.5 |
| Example 5 (0.5 µM) | 63.5 |
| Example 5 (1 µM) | 85.9 |

The above results show that the compounds of the present invention can inhibit the reduction in luciferase activity under the control of IL-2 promoter of Jurkat cells caused by the formation of PD-1/PD-L1 binding. That is, it is found that the compound of the present invention has an inhibitory effect of the reduced production amount of IL-2 in T-cells caused by the formation of PD-1/PD-L1 binding.

INDUSTRIAL APPLICABILITY

The compound of formula (I) or a pharmaceutically acceptable salt thereof of the present invention has an inhibitory effect of PD-L1 expression and/or an inhibitory effect of reduced production of IL-2, and are useful for the treatment of a disease associated with the reduced immune function caused by the formation of PD-1/PD-L1 binding (e.g., cancer and infection).

The invention claimed is:

1. A compound of formula (I):

or a pharmaceutically acceptable salt thereof, wherein $R^1$ and $R^2$ are each independently selected from the group consisting of hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro, amino, mono- or di-$C_{1-6}$ alkylamino, pentafluorosulfanyl, aryl and heteroaryl, wherein said aryl and heteroaryl may be optionally substituted with one group or the same or different two or more groups selected independently from the group consisting of halogen, hydroxy, cyano, nitro, amino, mono- or di-$C_{1-6}$ alkylamino, $C_{1-4}$ acyl, $C_{1-6}$ alkyl, $C_{1-6}$ haloalkyl, $C_{1-6}$ hydroxyalkyl, $C_{1-6}$ alkoxy, $C_{1-6}$ haloalkoxy and $C_{1-6}$ hydroxyalkoxy at any replaceable positions;

m is an integer of 1 to 5; and n is an integer of 1 to 5.

2. The compound according to claim 1 or a pharmaceutically acceptable salt thereof, wherein $R^1$ and $R^2$ are each independently selected from the group consisting of hydroxy, $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, nitro and pentafluorosulfanyl;

m is 1 or 2; and n is 1 or 2.

3. The compound according to claim 1 or a pharmaceutically acceptable salt thereof, wherein
$R^1$ is each independently selected from hydroxy, $C_{1-6}$ alkyl, $C_{1-6}$ alkoxy or nitro; and
$R^2$ is each independently selected from $C_{1-6}$ alkyl, $C_{1-6}$ haloalkyl, $C_{1-6}$ alkoxy or pentafluorosulfanyl.

4. The compound according to claim 1 or a pharmaceutically acceptable salt thereof, wherein $R^1$ is hydroxy, $C_{1-6}$ alkoxy or nitro which is linked at the 3- and/or 4-positions of the benzene ring.

5. The compound according to claim 1 or a pharmaceutically acceptable salt thereof, wherein $R^2$ is $C_{1-6}$ haloalkyl or pentafluorosulfanyl which is linked at the 4-position of the benzene ring.

6. The compound according to claim 1 or a pharmaceutically acceptable salt thereof selected from
1-(4-hydroxybenzoyl)-N-(4-(4-(trifluoromethyl)phenoxy) phenyl)piperidine-3-carboxamide,
1-(4-nitrobenzoyl)-N-(4-(4-(trifluoromethyl)phenoxy) phenyl)piperidine-3-carboxamide,
1-(4-hydroxy-3-methoxybenzoyl)-N-(4-(4-(trifluoromethyl)phenoxy)phenyl)piperidine-3-carboxamide,
1-(4-hydroxybenzoyl)-N-(4-(4-pentafluorosulfanyl) phenoxy)phenyl)piperidine-3-carboxamide,
1-(4-nitrobenzoyl)-N-(4-(4-(pentafluorosulfanyl) phenoxy)phenyl)piperidine-3-carboxamide, or
1-(4-hydroxy-3-methoxybenzoyl)-N-(4-(4-(pentafluorosulfanyl)phenoxy)phenyl)piperidine-3-carboxamide.

7. A pharmaceutical composition comprising the compound according to claim 1 or a pharmaceutically acceptable salt thereof and a pharmaceutically acceptable carrier.

8. A method of treating a disease associated with the reduced immune function caused by the formation of PD-1/PD-L1 binding, which comprises administering the compound according to claim 1 or a pharmaceutically acceptable salt thereof to a patient suffering from the disease.

9. The method according to claim 8, wherein the disease associated with the reduced immune function caused by the formation of PD-1/PD-L1 binding is cancer or infection.

10. The method according to claim 8, wherein the disease associated with the reduced immune function caused by the formation of PD-1/PD-L1 binding is cancer.

11. The method according to claim 10, wherein the cancer is skin cancer, brain tumor, lung cancer, gastric cancer, colorectal cancer, liver cancer, pancreatic cancer, renal cancer, adrenal cancer, biliary tract cancer, esophageal cancer, pharyngeal cancer, laryngeal cancer, oral cancer, bladder cancer, tongue cancer, thyroid cancer, breast cancer, prostate cancer, testicular cancer, uterine cancer, cervical cancer, ovarian cancer, osteosarcoma, chondrosarcoma, rhabdomyosarcoma, leiomyosarcoma, leukemia including adult T-cell leukemia, malignant lymphoma or multiple myeloma.

12. The method according to claim 8, wherein the disease associated with the reduced immune function caused by the formation of PD-1/PD-L1 binding is infection.

13. The method according to claim 12, wherein the infection is tuberculosis, Hepatitis B, Hepatitis C, Human Immunodeficiency Virus (HIV) infection, Human Papillomavirus (HPV) infection, Epstein-Barr virus (EBV) infection, Human cytomegalovirus (CMV) infection, Herpes simplex virus infection, or Human T-cell leukemia virus type 1 (HTLV-1) infection.

14. A method of inhibiting immune checkpoint, which comprises administering the compound according to claim 1 or a pharmaceutically acceptable salt thereof to a patient in need thereof.

15. The method according to claim 14, wherein the immune checkpoint is PD-L1.

16. A method of inhibiting PD-L1 expression, which comprises administering the compound according to claim 1 or a pharmaceutically acceptable salt thereof to a patient in need thereof.

17. A method of inhibiting reduced production of IL-2, which comprises administering the compound according to claim 1 or a pharmaceutically acceptable salt thereof to a patient in need thereof.

18. A method of enhancing the effect of a vaccine, which comprises administering the compound according to claim 1 or a pharmaceutically acceptable salt thereof to a patient in need thereof.

19. The method according to claim 11, wherein the skin cancer is malignant melanoma.

20. The method according to claim 11, wherein the brain tumor is glioblastoma.

* * * * *